United States Patent
Yu et al.

(10) Patent No.: US 9,116,142 B2
(45) Date of Patent: Aug. 25, 2015

(54) METHODS AND SYSTEMS FOR NONDISRUPTIVE LOADING OF REAGENTS IN A BODY FLUID WORKSTATION

(71) Applicant: SHENZHEN MINDRAY BIO-MEDICAL ELECTRONICS CO., LTD., Shenzhen (CN)

(72) Inventors: Huaibo Yu, Shenzhen (CN); Qiao Zou, Shenzhen (CN)

(73) Assignee: SHENZHEN MINDRAY BIO-MEDICAL ELECTRONICS CO., LTD., Shenzhen (CN)

( * ) Notice: Subject to any disclaimer, the term of this patent is extended or adjusted under 35 U.S.C. 154(b) by 42 days.

(21) Appl. No.: 14/054,469

(22) Filed: Oct. 15, 2013

(65) Prior Publication Data

US 2014/0038298 A1 Feb. 6, 2014

Related U.S. Application Data

(63) Continuation of application No. PCT/CN2011/072886, filed on Apr. 15, 2011.

(51) Int. Cl.
    G01N 35/02      (2006.01)
    G01N 35/10      (2006.01)
    G01N 35/00      (2006.01)

(52) U.S. Cl.
    CPC ........ *G01N 35/1002* (2013.01); *G01N 35/0092* (2013.01); *Y10T 436/113332* (2015.01); *Y10T 436/114165* (2015.01); *Y10T 436/115831* (2015.01); *Y10T 436/12* (2015.01)

(58) Field of Classification Search
    CPC ............ G01N 35/00; G01N 35/00584; G01N 35/0092; G01N 35/02; G01N 35/1002; Y10T 436/11; Y10T 436/114165; Y10T 436/115831; Y10T 436/113332; Y10T 436/12
    USPC .......... 436/43, 47, 48, 50, 55; 422/63, 65, 67, 422/68.1; 435/287.1, 287.3
    See application file for complete search history.

(56) References Cited

U.S. PATENT DOCUMENTS

| | | | |
|---|---|---|---|
| 5,368,041 A | 11/1994 | Shambroom | |
| 5,380,488 A | 1/1995 | Wakatake | |
| 5,428,993 A * | 7/1995 | Kobashi | 73/149 |
| 5,902,549 A * | 5/1999 | Mimura et al. | 422/65 |
| 6,236,874 B1 | 5/2001 | Devlin et al. | |

(Continued)

FOREIGN PATENT DOCUMENTS

| | | |
|---|---|---|
| CN | 1168471 A | 12/1997 |
| CN | 101031235 A | 9/2007 |

(Continued)

*Primary Examiner* — Maureen Wallenhorst
(74) *Attorney, Agent, or Firm* — Kory D. Christensen; Stoel Rives LLP

(57) ABSTRACT

A method of nondisruptive loading of reagents in a body fluid workstation including a plurality of analyzers, including: receiving application information to a first analyzer which needs loading of a reagent; loading the reagent into the first analyzer; controlling the first analyzer to pause dispensing of the reagent at a determined time; and controlling one or more other analyzers in the body fluid workstation to continue testing, wherein controlling the one or more other analyzers includes adjusting a test sequence of one or more sample racks in the one or more other analyzers subsequent to the first analyzer, and dispatching the one or more sample racks according to the adjusted test sequence.

22 Claims, 2 Drawing Sheets

(56) References Cited

U.S. PATENT DOCUMENTS

| | | | |
|---|---|---|---|
| 7,556,771 B2 * | 7/2009 | Nakamura et al. | 422/67 |
| 2004/0253146 A1 * | 12/2004 | Shiba et al. | 422/64 |
| 2008/0056944 A1 * | 3/2008 | Nakamura et al. | 422/67 |
| 2008/0102528 A1 * | 5/2008 | Xu et al. | 436/47 |

FOREIGN PATENT DOCUMENTS

| | | |
|---|---|---|
| CN | 101135692 A | 3/2008 |
| CN | 101169450 A | 4/2008 |
| EP | 0558212 A2 | 9/1993 |

\* cited by examiner

METHODS AND SYSTEMS FOR NONDISRUPTIVE LOADING OF REAGENTS IN A BODY FLUID WORKSTATION

TECHNICAL FIELD

This disclosure relates to a body fluid workstation and, more particularly, to a body fluid workstation with multiple analyzers that can implement nondisruptive loading of reagents without shutting down one or more of the analyzers.

BACKGROUND

A biochemical analyzer is one common type of body fluid analyzer. A biochemical analyzer may include a dispensing mechanism, a reagent disk, a sample disk, and a reaction disk. The sample disk is used for holding a sample container that contains a sample for testing. The reagent disk is used for holding a reagent container that contains a reagent. The reaction disk is used for holding a cuvette. By controlling the rotation of the reagent disk, the sample disk, and the reaction disk, a dispensing mechanism dispenses sample and reagent into the cuvette. Testing and analysis are executed after the sample and reagent are mixed and reacted.

With the proliferation of body fluid analyzer applications and the increase in the number of samples to be tested, integrated body fluid workstations have appeared. These body fluid workstations may be used for biochemical analysis as biochemical analysis assembly line workstations. They may also be used for fluid analysis as body fluid workstations for blood, serum, urine, or other body fluid testing. Such body fluid workstations may include two or more analyzers, each analyzer including a dispensing mechanism, a reagent disk, and a reaction disk. In addition, such body fluid workstations may adopt a unified conveyance track, which is used for conveying sample racks that hold sample containers for testing. The sample racks are conveyed to a determined analyzer for dispensing and testing by the track.

Body fluid workstations require a high degree of automation, fast testing speeds, and the ability to process many samples. Because hospitals process many samples at a given time, there are also many reagents used in the testing process. In a fluid workstation, the doctor usually adds sufficient reagents at the beginning of a day so as to handle one day's consumption.

Advantages of adding reagents in this way include that it is easy and convenient for the doctor. However, there are also drawbacks. If a particular reagent is exhausted during testing, the testing cannot be paused, and the system must wait until other sample(s) have finished testing. Thereafter, the doctor must add more of the reagent that ran out and test the corresponding sample again, wasting the doctor's time. This may be of particular concern in emergency situations. If there is insufficient reagent during testing, the analyzer must be stopped to add the reagent, resulting in delayed reporting of test results.

DETAILED DESCRIPTION

This disclosure includes systems and methods for operating a fluid workstation including multiple analyzers and nondisruptively loading reagents, i.e., reagents that can be loaded without shutting down one or more of the analyzers, allowing them to continue testing. Utilizing the present disclosure, a user of a body fluid workstation can add reagent in one or more analyzers without influencing the other analyzers, thereby avoiding retesting a sample due to lack of a reagent, and stopping and restarting the workstation. This method will save time and ensure the timely output of emergency test reports.

Figure 1:
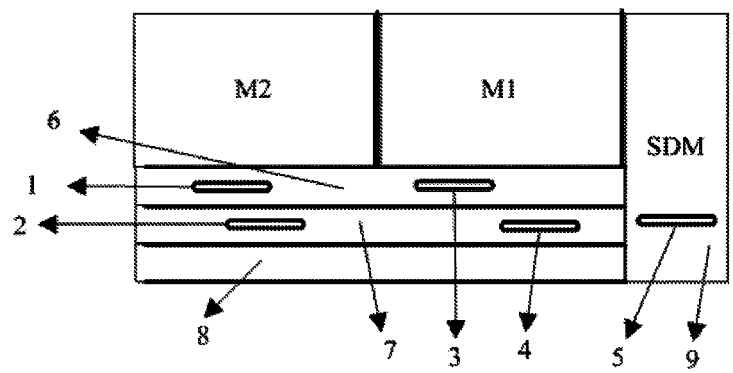
FIG. 1 is a schematic diagram of an embodiment of a body fluid workstation.

Referring to FIG. 1, a body fluid workstation includes a sample loading mechanism and at least two analyzers. The illustrated embodiment includes two analyzers, labeled M1 and M2. In other embodiments, there may be three or more analyzers, and a sample loading mechanism may include a sample loading track and a sample rack driving mechanism (not shown). The sample loading track may be used for holding a sample rack and restricting the moving track of the sample rack, the sample loading track include the first track 6 and a second sample track 7.

The sample rack driving mechanism may be used for moving a sample rack to a determined place according to dispatching instructions. For example, the sample rack driving mechanism may be used for moving a sample rack to a test position of one of the analyzers for testing according to the dispatching instructions. The sample rack driving mechanism may be embodied, for example, as a transmission belt, a putter, or a push plate.

Each analyzer may include a dispensing mechanism, a reagent disk, and a reaction disk. The reagent disk may be used for holding the reagent container including reaction reagent, which is used for testing. The reaction disk may be used for holding a cuvette. The analyzer may dispense samples and reagents for a sample rack, which is moved to the determined position, for example, by a sample dispensing mechanism. The sample dispensing mechanism dispenses samples and reagents to the cuvette for testing.

According to one embodiment, if the system needs to pause testing of a particular analyzer (e.g., M1 or M2) of the body fluid workstation, the system may ensure that the unaffected analyzer(s) continue to test. As described in greater detail below, according to the user's loading application information, the system may decide, for example, to pause dispatching of a sample rack for an analyzer that needs nondisruptive loading of one or more reagents. The sample rack of the other analyzer(s) may continue to dispatch.

In one embodiment, according to application information input by the user, the loading system of the workstation will pause one analyzer at a determined moment to allow nondisruptive loading of reagent(s), as well as control the other analyzer(s) to allow testing to continue. For example, after the loading system receives loading application information, it controls the analyzer corresponding to the loading application information to pause the dispensing operation. In another embodiment, after the loading system receives loading application information, according to the current test status of the analyzer corresponding to the loading application information, the system will decide when to control the analyzer to pause the dispensing operation. When a user inputs loading application information, the loading system checks the test status of the analyzer which corresponds to the loading application information when the analyzer is testing. It should be determined whether the analyzer corresponding to the loading application information meets the condition. When the analyzer meets the condition, it pauses the dispensing operation. When the user inputs conveyance instructions to the analyzer corresponding to the loading application information, the paused analyzer may continue to test.

In one embodiment, the loading system may also check the test items and test sequence of each sample rack, determine whether a sample rack is the first sample rack that the analyzer corresponding to the loading application information is testing or will test, and, if it is, generate a dispatch construction of the first sample rack, such that the sample loading mechanism will pause dispatch of the first sample rack according to dispatch construction. For example, the first sample rack may be paused in the first sample loading track while sample racks of other analyzers continue to dispatch. A hot loading system can be made in one or more integrated chips, or in separate hardware.

In one embodiment, the loading system of the body fluid workstation includes an input unit, a testing unit, and a sample loading unit. The functionality of various units may include steps, which may be embodied in machine-executable instructions to be executed by a general-purpose or special-purpose computer (or other electronic device). Alternatively, the steps may be performed by hardware components that include specific logic for performing the steps, or by a combination of hardware, software, and/or firmware.

The input unit is configured for receiving loading application information for the analyzer which needs nondisruptive loading of one or more reagents. The application information is input by one or more users. The testing unit includes a pausing sub-unit configured for responding to the loading application information, controlling the analyzer corresponding to the loading application information to pause testing, and controlling the other analyzer(s) of the body fluid workstation to continue testing. The sample loading unit is configured for checking test items and the test sequence of each sample rack, determining whether a sample rack is the first sample rack to be tested by the analyzer corresponding to the loading application information. If it is, the sample loading unit will pause dispatching the first sample rack. The first sample rack is held in the sample loading track of the analyzer corresponding to the loading application information while waiting to be tested, and the other analyzers continue to dispatch.

In other embodiments, the testing unit includes an adjustment sub-unit. The adjustment sub-unit is configured for adjusting the test sequence of the sample rack corresponding to the analyzer which comes after the analyzer corresponding to the loading application information. The sample loading unit may dispatch the sample rack according to this changed sequence.

In another embodiment, the adjustment sub-unit includes a first check unit and a test sequence change unit. The first check unit is configured for determining, after the first sample rack is tested by the analyzer corresponding to the loading application information, whether subsequent analyzers of the body fluid workstation need to test that sample rack. The test sequence change unit is configured for changing the test sequence of the first sample rack in subsequent analyzers when the first rack needs subsequent analyzers of body fluid workstation to test, the test sequence of the first sample rack in subsequent analyzer is adjusted afterward. The sample loading unit dispatches the sample rack according to the adjusted test sequence. The second sample rack, which is tested in the subsequent analyzer before the first sample rack, will be conveyed to the test position of the subsequent analyzer by the second sample loading track, which is different from the first sample loading track.

In one embodiment, the adjustment sub-unit includes a second check unit and test sequence change unit, the second check unit is configured for monitoring the test sequence of a sample rack on a sequence analyzer, which test sequence of the analyzer is corresponding to the loading application information. When the first sample rack is going to be tested, the adjustment sub-unit checks the test status of the first sample rack in the analyzer corresponding to the loading application information. The test sequence change unit is configured for changing the test sequence of the first sample rack in the subsequent analyzer when the test of the first sample rack is not finished in the analyzer corresponding to the loading application information, and to adjust the test sequence of the first sample rack in the subsequent analyzers backwards. The sample loading unit dispatches the sample rack according to the adjusted test sequence. After adjustment, the second sample rack, which tests in the subsequent analyzer before the first sample rack, will be conveyed to the test position of the subsequent analyzer by the second sample loading track, which is different from the first sample loading track.

To control the residual reagent, the loading system also includes a reagent loading unit and residual reagent calculation unit. The reagent loading unit is configured for acquiring parameters relating to liquid level detection and the test items. The residual reagent calculation unit is configured for calculating a test number of residual reagents according to the parameters of the liquid level detection and test items.

In order to inform users concerning the residual reagent, the loading system also includes a reagent loading inform unit. The reagent loading inform unit is configured for inputting the test number of each residual reagent to display and/or compare the test number of the residual reagent to the test number of the application. When the test number of a residual reagent is less than the test number of the application, an alarm and/or display of the reagent may be generated in a predetermined manner.

Figure 2:
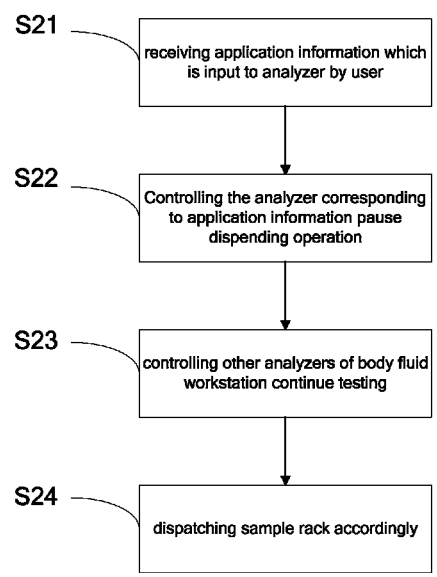
FIG. 2 is a flow chart of an embodiment of nondisruptive loading of a reagent.

FIG. 2 shows a method of nondisruptively loading reagents. At Step S21, application information is received and input into the analyzer by a user. Utilizing a display interface, the user can decide whether to nondisruptively load a certain reagent and assign which analyzer to load the reagent into, and then can input the loading application information of the analyzer via the interface.

At Step S22, the loading system responds to the application information of the body fluid workstation and controls the first analyzer corresponding to the loading application information to pause a dispensing operation. When pausing the dispensing operation of the first analyzer, the test status of the first analyzer could be considered, or not be considered, according to various embodiments. For example, in one embodiment, after receiving the loading application information, the loading system may control the first analyzer to pause dispensing of a reagent immediately, without considering the test status of the first analyzer. In this situation, the reagent disk and the reagent dispensing mechanism pause operation, but the reaction disk, the sample disk, and the sample dispensing mechanism may continue to work.

In another embodiment, after the loading system receives the loading application information, it may control pausing of the dispensing operation of the analyzer corresponding to the loading application information according to the test status of the analyzer, as follows: The loading system may acquire the test status of the first analyzer. When the first analyzer is testing, the system determines whether the first analyzer meets the pause condition. If it does not meet the condition, the system causes the first analyzer to pause immediately. When the analyzer meets the condition, the system controls the first analyzer to pause the dispensing reagent operation. The pause condition could be, for example, that all reagents have been dispensed into a cuvette to which a part of the reagents have been added. For example, when receiving loading application information, the first analyzer has dispensed the first reagent to five cuvettes, but has not dispensed the sample and the other reagent. In this condition, to a single reagent item, the loading system continues to control the pause operation of the reagent disk and the dispensing operation of the first analyzer. However, the reaction disk, the sample disk, and the sample dispensing mechanism continue to work, so as to finish the adding sample operation. To a multi-reagent item, the loading system continues dispensing sample and the other reagent to the five cuvettes of the first analyzer. After dispensing the reagent to the five cuvettes, it then controls pausing of the dispensing operation of the first analyzer, so as to avoid reagent waste or inaccurate test results.

At Step S23, the loading system controls the other analyzers of body fluid workstation to continue testing. After the loading system response to the application information, the other analyzers of the workstation are not influenced. Thus, except for the first analyzer corresponding to the loading application information, all analyzers continue to work.

At Step S24, the loading system dispatches the sample rack accordingly. The loading system acquires and checks the test item and the test sequence of each sample rack. The loading system determines whether a sample rack is the first sample rack that the analyzer corresponding to the application information is testing or will test. If so, the loading system pauses the first sample rack dispatch. The first sample rack is paused in the sample loading track and holds the first analyzer test, but allows the sample racks of the other analyzers to continue dispatching. After receiving the loading application information, the first sample rack is paused at the original position, waiting for testing until the paused analyzer is restarted. The other analyzers continue to dispatch, allowing them to continue testing.

The sequence of Steps S22, S23, and S24 could be changed while realizing the same effect.

In actual operation, the analyzer corresponding to the loading application information could be the first analyzer along the sample loading track, or could be positioned among analyzers, or could be the last analyzer. The test sequence of a sample rack is usually based on the order of the analyzers along the sample loading track; however, sample rack pass which analyzer is depend on test item and reagent placement, the sample rack may not passes all analyzer. To the first sample rack, it need pass the first analyzer, and also may need test by analyzer which is after the first analyzer. When the first sample rack need test by the subsequent analyzer which is after the first analyzer, the first sample rack is paused in the first analyzer because of loading reagent hot, the first sample rack can not arrive at subsequent analyzer according to a predetermined time, this may cause subsequent analyzer can not test normally. And some sample rack may not need test by the first analyzer, but need test by subsequent analyzer, but the test sequence of the sample rack is after the first sample rack, if by original dispatch way, it will cause unnecessarily wait and congestion of following sample rack.

In the present embodiment, by controlling each analyzer and dispatching each sample rack, controlling the first analyzer to pause which corresponds to the loading application information, the other, uninfluenced analyzer does not pause testing. Likewise, dispatching of sample rack is paused which need testing by the first analyzer, while the other sample racks which do not need testing by the first analyzer continue to be dispatched. The sample rack is conveyed to the test position according to the test time, so that the other, uninfluenced analyzer can test normally.

In order to ensure the accuracy of the test of the subsequent analyzer, when dispatching the other sample rack which does not need testing by the first analyzer, the loading system changes the test sequence of the sample rack of the subsequent analyzer which is after the analyzer corresponding to loading application information. For example, it changes the test sequence of the first sample rack in the subsequent analyzer afterwards, and dispatches the sample rack according to the adjusted test sequence. The sample rack which is after the first sample rack is tested in the subsequent analyzer earlier than the first sample rack. Because the test sequence of the sample rack of subsequent analyzer and dispatch way are changed at the same time, it is ensured that the test of subsequent analyzer is continuous and correct.

There are many ways to change test sequence of subsequent analyzer. In one embodiment, the system may determine whether the first rack needs testing by the subsequent analyzer of the body fluid station after the first sample rack is tested by the analyzer corresponding to the loading application information. If it is, the system changes the test sequence of the first sample rack in subsequent analyzer, the test sequence of the first sample rack in the subsequent analyzer is adjusted afterward. In another embodiment, system real-time monitors the test sequence of the sample rack in subsequent analyzer which is after the analyzer corresponding to the loading application information, when the first sample rack is going to be test (for example, there is some time or there are several sample racks to test), checking the test status of the first sample rack in the analyzer corresponding to the loading application information. If the test is not finished, the system changes the test sequence of the first sample rack in subsequent analyzer, adjusting the test sequence of the first sample rack in subsequent analyzer backwards. Adjusting the test sequence of sample rack in subsequent analyzer afterward, the system dispatches the sample rack according to the adjusted test sequence. The second sample rack which tested in the subsequent analyzer before the first sample rack will be conveyed to the test position of the subsequent analyzer by the second sample loading track, which is different from the first sample loading track.

Figure 3:
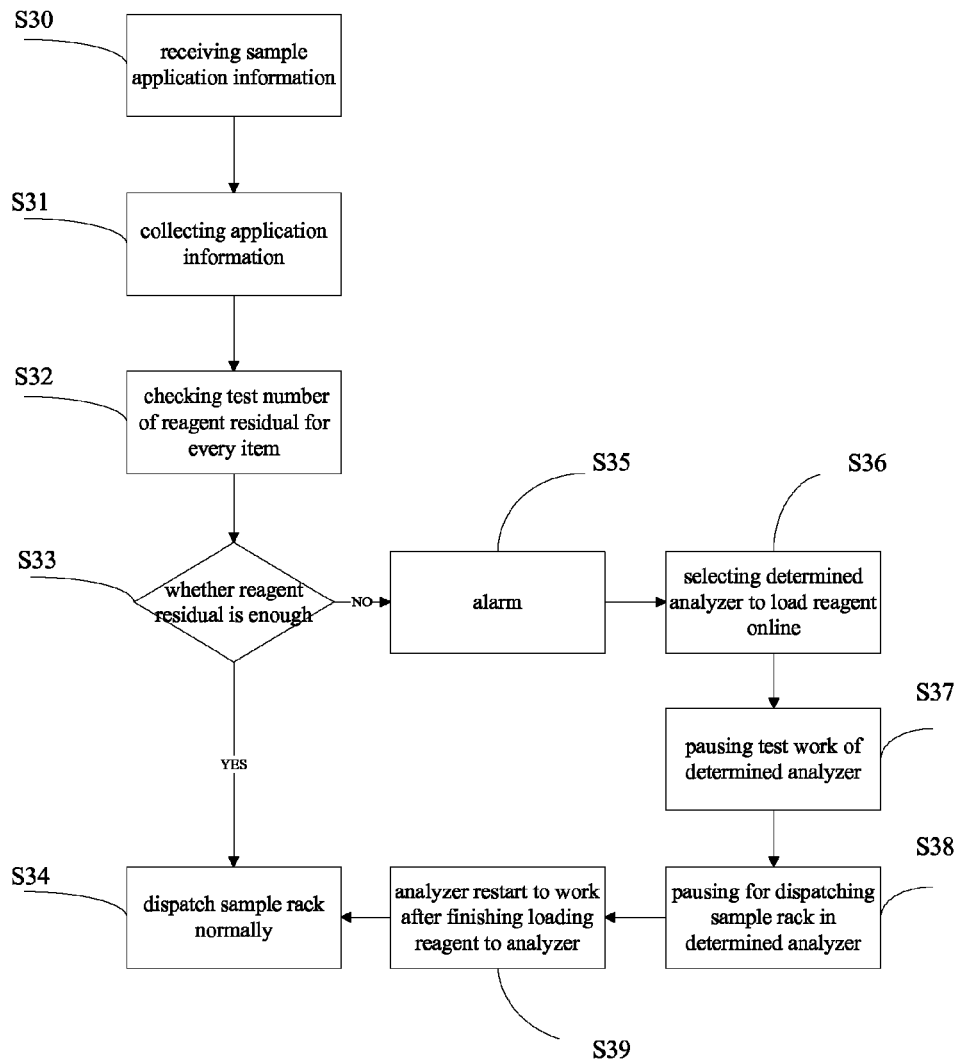
FIG. 3 is a flow chart of an embodiment of nondisruptive loading of a reagent.

FIG. 3 illustrates a reagent loading method including the following steps.

In Step S30, the system collects user application information, a sample number, and a select item name of the application. The item of application is the object for collection. Usually, user inputs application information of a sample. The application item of each sample may not be the same. After the input work is finished, the user may not remember to apply how many times for each item.

In Step S31, according to application information input by step S30, the system collect the number of times for each item according to the item name.

In Step S32, the system calculates a test number of residual reagent for every item automatically, detects the reagent liquid height by liquid detect device, acquires parameters of the liquid height detection and the test item, then, calculates a test number of every residual reagent according to parameters of the liquid height detection and the test item. When displaying the test number of every residual reagent, the test number of every residual reagent of every analyzer can be display on each analyzer, respectively, or the test number of every residual reagent of all analyzers is collected and display.

In step S33, the system may determine whether the residual reagent is enough, that is, determine whether the test number of the residual reagent is sufficient to meet the condition of nondisruptive loading the reagent. In one embodiment, the system may determine whether the test number of the residual reagent of every item meets the test number of the application. If the test number of the residual reagent is more than the test number of the application, the method may proceed to Step S34 directly and dispatch the sample rack normally. However, if the test number of residual reagent is less than the test number of the application, the method may proceed to Step S35 directly and the system inform the user to loading the reagent. In another embodiment, the system may determine whether the test number of each residual reagent is greater than a determined threshold (e.g., 2 times). If it is, the method may proceed to Step S24 to dispatch sample the rack normally. If not, the system may inform the user to load the reagent.

In Step S35, the system may generate an alarm, for example, displaying the reagent which needs to be loaded by color, flicker, or highlighting, or by alarm sounds, or display tips that point the user to which unit of the workstation need loading of the reagent. In other embodiment, the comparison of Step S33 can be omitted. Instead, the system may display the test number of each residual reagent directly and constantly updated. The user may check and decide whether to load the reagent according to the test numbers of each residual reagent.

In Step S36, the user can decide whether to load the reagent according to the alarm, tips, etc. of Step S35, select the analyzer needing reagent(s) by man-machine interface, and input the loading application information. If there is only one analyzer that needs to load reagent, the user may select the only one analyzer to nondisruptive load reagent. If all of the analyzers need to load reagent(s), the user may select all of analyzers to nondisruptive load reagent. In certain circumstance, even if the user is informed about the need to load reagents in a certain analyzer, the user can also decide not to load the reagents by not inputting the application information. For example, there is X reagent on both the first analyzer and the second analyzer, when X reagent of the first analyzer is going to be exhausted, and X reagent needs to be loaded into the first analyzer, the user may decide to not input application information to the first analyzer according to test status of sample rack and residual reagent of the second analyzer. Instead, when the second analyzer is also needed to load reagent X, the user then inputs application information to one of the two analyzer or to both.

In Step S37, the testing unit will pause the test work of the analyzer corresponding to the loading application information while, at the same time, keeping other analyzers which do not need to load reagents to continue to work. When the first sample rack also needs a subsequent analyzer to test after pass the first analyzer corresponding to loading application information, change test sequence of the first sample rack in the subsequent analyzer, adjust test sequence of the first sample rack in the subsequent analyzer backwards, so as to change test sequence of sample rack in the subsequent analyzer. Alternatively, when the first sample rack is going to be tested, the system may check the test status of the first sample rack in the analyzer corresponding to the loading application information. When the test of the first sample rack is not finished, the system may adjust the test sequence of the first sample rack in the subsequent analyzer backwards, so as to change the test sequence of sample rack in the subsequent analyzer.

In Step S38, the sample loading unit will pause the dispatch of the sample rack in analyzer corresponding to the loading application information. The other analyzer will continue to dispatch normally. The sample rack loading unit will check the test items and the test sequence of each sample rack, determining whether the sample rack is the first rack which is testing or going to be tested in the analyzer corresponding to the loading application information. If it is, the system pauses dispatch of the first sample rack and keeps other analyzer going. If the test sequence sample rack in subsequent analyzer is adjusted, the system dispatches the sample rack according to the adjusted test sequence. After adjustment, the second sample rack may go to testing in a following sample rack earlier than the first sample rack is dispatched to the second sample loading track, which is different from the first sample loading track. The system may control movement of the second sample rack to the test position of the subsequent analyzer by the second sample loading track.

In Step S39, after finishing the loading of reagent into the analyzer, in response to user input, the analyzer may restart and the test work may continue, with the sample rack dispatching normally.

In certain embodiments, Step S37 and Step S38 can be exchanged, and the sequence of S37 and S38 can be changed.

Because the system is checking the residual reagent constantly according to the test application information input by the user, when determining that a certain residual reagent is not enough for adding in a certain cuvette, reagent should not be added to the cuvette. Therefore, is convenient to control pausing the dispensing of reagent of the first analyzer. For example, after receiving application of the nondisruptive loading, the test status of the first analyzer is testing, controlling the first analyzer does not pause until all cuvettes which have reagent being added finished the dispensing reagent operation and do not need to consider whether the residual reagent is insufficient Referring again to FIG. 1, a body fluid workstation may include, as an example, two analyzers, although three or more analyzers is similar. Along the direction of loading the sample, analyzer M2 is after analyzer M1, so M2 is the "subsequent" analyzer. The sample loading track includes the first sample loading track 6 and the second sample loading track 7. There are test positions in the first sample loading track 6 and the second sample loading track 7 corresponding to the analyzer M1 and the analyzer M2 separately. Sample racks 1, 2, 3, 4, 5 are conveyed to the first sample loading track 6 and sample loading track 7 by the sample put area and the sample retrieve area 9. For example, a sample which needs to be tested by analyzer M1 will arrive at analyzer M1 and analyzer M2 by the first sample loading track. Sample 1, 3, may only need to tested by analyzer M2, and arrive at M2 directly by the second sample loading track, e.g., sample racks 2, 5. After testing, the sample rack will be returned to the put area and the sample retrieve area 9.

When testing, if user finds analyzer M1 needs to load a reagent, the user may selectively initiate a command to load the reagent to analyzer M1. After the analyzer M1 is selected to load the reagent, testing of analyzer M1 is paused. However, testing of analyzer M2 continues, and sample rack 3 needs to be tested by analyzer M1, so sample rack 3 is paused in the first sample loading track 6. If the sample rack also needs testing by analyzer M2, to avoid sample rack 3 having not yet arrived at the test position of analyzer M2, after the sample rack 1 and sample rack 2 are tested by the analyzer M2, it is needed to adjust the test sequence of the sample rack in analyzer M2 and adjust the test sequence of sample rack 3 backwards, then dispatch the sample rack according to the adjusted test sequence of the sample rack. If sample rack 4 does not need test by analyzer M1, the test sequence of sample rack 4 will be adjusted in front of the sample rack 3. The sample rack 4 may be driven by the sample rack driving device of sample loading mechanism to the second sample loading track 7, and arrive at the test position of analyzer M2 by the second sample loading track 7, or go to the second sample loading track 7 initially, then be moved from the second sample loading track 7 to the first sample loading track 6, and pause in the test position of analyzer M2 in the first sample loading track 6. If sample rack 4 is in the first sample loading track 6 originally, then the sample rack 4 is conveyed to the second sample loading track 7 initially, then arrives at the test position of analyzer M2 by the second sample loading track 7. If sample rack 4 also needs testing by analyzer M1, then sample rack 4 continues to wait for testing in the first sample loading track 6, and does not need to adjust the test sequence of sample rack 5 in analyzer M2 in front of sample rack 3, and sample rack 5 is finished testing by analyzer M1, driving sample rack 5 to the second sample loading track 7 by the sample rack driving device of the sample loading mechanism and arrives at test position of analyzer M2 by the second sample loading track 7.

In FIG. 1, the first sample loading track is closed to the analyzer. In another embodiment, the position of first sample loading track 6 and the second sample loading track 7 may be changed.

Those having skill in the art will appreciate that many changes may be made to the details of the above-described embodiments without departing from the underlying principles of the invention. The scope of the present invention should, therefore, be determined only by the following claims.

What is claimed is:

1. A method of nondisruptive loading of reagents in a body fluid workstation comprising a plurality of analyzers, including: receiving application information to a first analyzer which needs loading of a reagent; loading the reagent into the first analyzer; controlling the first analyzer to pause dispensing of the reagent at a determined time; and controlling one or more other analyzers in the body fluid workstation to continue testing, wherein controlling the one or more other analyzers comprises adjusting a test sequence of one or more sample racks in the one or more other analyzers subsequent to the first analyzer, and dispatching the one or more sample racks according to the adjusted test sequence.

2. The method of claim 1, wherein controlling the first analyzer comprises: when the first analyzer is testing, determining whether the first analyzer satisfies a pause condition; if the first analyzer meets the pause condition, controlling the first analyzer to pause dispensing the reagent.

3. The method of claim 2, wherein the pause condition is met when all of needed reagents have been dispensed into a cuvette if part of the needed reagents have already been added into the cuvette.

4. The method of claim 1, wherein, after receiving the application information, the method further includes a sample rack dispatching step comprising: checking a test item performed on samples that are located in every sample rack and a test sequence of every sample rack; determining whether a sample rack is a first sample rack that the first analyzer is testing or will test; and if so, pausing dispatching of the first sample rack and allowing the one or more sample racks tested on the one or more other analyzers to continue to dispatch.

5. The method of claim 4, wherein adjusting the test sequence includes: determining whether the first sample rack also needs to be analyzed by the one or more other analyzers of the body fluid workstation after being tested by the first analyzer; if the first sample rack also needs to be analyzed by the one or more other analyzers, changing a test sequence of the first sample rack in a subsequent analyzer, the test sequence of the first sample rack in the subsequent analyzer is adjusted afterward.

6. The method of claim 5, wherein dispatching the one or more other sample racks according to the adjusted test sequence includes: if a second sample rack is tested in the subsequent analyzer before the first sample rack is tested in the subsequent analyzer, the second rack is conveyed to a test position of the subsequent analyzer by a second sample loading track which is different from a first sample loading track for conveying the first sample rack.

7. The method of claim 4, wherein adjusting the test sequence includes: monitoring a sequence of sample racks in an analyzer subsequent to the first analyzer; when the subsequent analyzer is going to test the first sample rack, checking whether the first analyzer is still testing; and if the first analyzer is still testing, changing a test sequence of the first sample rack in the subsequent analyzer, wherein the test sequence of the first sample rack in the subsequent analyzer is adjusted afterward.

8. The method of claim 1, wherein receiving application information of the first analyzer is preceded by: acquiring parameters of liquid height of reagents in every analyzer and a test item performed on samples in every analyzer; calculating a test number for every residual reagent according to the parameters; outputting the test number that is performed with every residual reagent in every analyzer to a display; and determining whether the test number of every residual reagent meets a condition of loading the reagent, the condition of loading the reagent comprises that the test number of the residual reagents is less than the test number of the application, and if the condition is met, notifying a user.

9. The method of claim 1, wherein after the step of controlling the first analyzer to pause dispensing, the method includes: receiving an instruction of restarting testing of the first analyzer; and controlling the first analyzer to restart testing and dispatch sample racks normally.

10. A system for nondisruptive loading of reagents in a body fluid workstation comprising a plurality of analyzers, including: an input unit for receiving application information of a first analyzer which needs loading of a reagent; a testing unit including a pausing sub-unit, the pausing sub-unit configured for responding to the application information, controlling the first analyzer to pause a reagent dispensing operation at a determined time, and controlling one or more other analyzers of the body fluid workstation to continue testing; a sample loading unit configured for checking one or more test items performed on samples that are located on every sample rack and a test sequence of every sample rack, determining whether a sample rack is a first sample rack that the first analyzer is testing or will test, and, if so, pausing dispatch of the first sample rack and allowing the one or more other analyzers of the body fluid workstation to continue to dispatch sample racks, wherein the test unit includes an adjusting sub-module, the adjusting sub-module configured for adjusting a test sequence of one or more sample racks corresponding to an analyzer subsequent to the first analyzer, and the sample loading unit dispatches the one or more sample racks according to the adjusted test sequence.

11. The system of claim 10, wherein the pausing sub-unit is configured for: determining whether the first analyzer is testing; if so, determining whether the first analyzer meets a pause condition; and when the condition is met, controlling the first analyzer to pause dispensing a reagent.

12. The system of claim 11, wherein the pause condition is met when all needed reagents have been dispensed into a cuvette if part of reagents have already been added into the cuvette.

13. The system of claim 10, wherein the adjusting sub-module includes: a first check unit configured for determining whether the first sample rack needs to be tested by a subsequent analyzer of the body fluid workstation after the first sample rack is tested by the first analyzer; a test sequence change unit configured for changing a test sequence of the first sample rack in the subsequent analyzer if the first sample rack needs to be tested by the subsequent analyzer, the test sequence of the first sample rack in the subsequent analyzer is adjusted afterward; a sample loading unit configured for dispatching the first sample rack according to the adjusted test sequence, wherein if a second sample rack is tested in the subsequent analyzer before the first sample rack is tested in the subsequent analyzer, the second sample rack is conveyed to a test position of the subsequent analyzer by a second sample loading track which is different from a first sample loading track for conveying the first sample rack; or, a second check unit configured for monitoring a test sequence of a sample rack which is after the first analyzer and, when the first sample rack is going to test, checking a test status of the first sample rack in the first analyzer; a test sequence change unit configured for changing the test sequence of the first sample rack in the subsequent analyzer and, when the test of the first sample rack is not finished in the first analyzer, adjusting the test sequence of the first sample rack in the subsequent analyzer afterward; and a sample loading unit configured for dispatching the first sample rack according to the adjusted test sequence, wherein if a second sample rack is tested in the subsequent analyzer before the first sample rack is tested in the subsequent analyzer, the second sample rack is conveyed to a test position of the subsequent analyzer by the second sample loading track which is different from a first sample loading track for conveying the first sample rack.

14. The system of claim 10, further comprising: a reagent loading unit configured for acquiring one or more parameters of liquid height of reagent in every analyzer and test items performed on samples in every analyzer; a residual reagent calculation unit configured for calculating a test number of remaining residual reagents in the first analyzer according to the parameters; and a reagent loading inform unit configured for comparing the test number that is performed with the remaining residual reagents in every analyzer to the test number of an application, and if the test number of the remaining residual reagents is less than the test number of the application, notifying a user.

15. A body fluid workstation including: a sample loading mechanism including a sample loading track and a sample rack driving mechanism, the sample loading track configured for holding a sample rack, and the sample rack driving mechanism configured for moving the sample rack to a determined place according to dispatching instructions; at least two analyzers having a determined test sequence, each analyzer including a dispensing mechanism, a reagent disk and a reaction disk, and an analyzer testing samples of the sample rack which is conveyed to a determined position; and a loading system configured for: responding to application information for loading reagent into a first analyzer needing reagent, controlling the first analyzer to pause dispensing of the reagent at a determined time, and controlling one or more other analyzers of the body fluid workstation to continue testing, wherein the loading system is configured to adjust a test sequence of one or more sample racks in the one or more other analyzers and to dispatch the one or more sample racks according to the adjusted test sequence.

16. The body fluid workstation of claim 15, wherein the loading system: after receiving application information, determines whether the first analyzer is testing; when the first analyzer is testing, determines whether the first analyzer meets a pause condition; and when the pause condition is met, controls the analyzer corresponding to the application information to pause dispensing of the reagent.

17. The body fluid workstation of claim 16, wherein the pause condition is when all needed reagents have been dispensed into a cuvette if a part of needed reagents have already been dispensed into the cuvette.

18. The body fluid workstation of claim 15, wherein the loading system: checks one or more test items that are performed on the samples of the sample rack in the first analyzer and a test sequence of every sample rack; determines whether the sample rack is a first sample rack that the first analyzer is testing or will test; and generates a dispatching instruction to the first sample rack that the first analyzer is testing or will test, wherein the sample loading mechanism pauses dispatching of the first sample rack according to the dispatching instruction while the sample racks of the one or more other analyzers continue to dispatch.

19. The body fluid workstation of claim 18, wherein the loading system is configured to determine whether the first sample rack also needs to be tested by the one or more analyzers of the body fluid workstation and, if so, the loading system changes a test sequence of the first sample rack in the subsequent analyzer, the test sequence of the first sample rack in the subsequent analyzer is adjusted afterward.

20. The body fluid workstation of claim 19, further comprising a first sample loading track and a second sample loading track, wherein the loading system is configured to generate a second dispatching instruction according to the adjusted test sequence of the sample rack in the subsequent analyzer, if a second sample rack is tested in the subsequent analyzer before the first sample rack is tested in the subsequent analyzer, controlling the sample loading driving mechanism of the sample loading mechanism driving the second sample rack by the second sample loading track which is different from the first sample loading track for conveying the first sample rack.

21. The body fluid workstation of claim 18, wherein the loading system is configured to monitoring a sequence of sample racks in an analyzer subsequent to the first analyzer; when the subsequent analyzer is going to test the first sample rack, checking whether the first analyzer is still testing; and if the first analyzer is still testing, changing a test sequence of the first sample rack in the subsequent analyzer, wherein the test sequence of the first sample rack in the subsequent analyzer is adjusted afterward.

22. The body fluid workstation of claim 15, wherein the loading system is configured for: acquiring parameters of liquid level of reagent in every analyzer and test items that are performed on the samples in each analyzer; calculating a test number of each residual reagent according to the parameters; and displaying the test number that is performed with the remaining residual reagent in each analyzer.

* * * * *